US011758996B2

(12) United States Patent
Thompson

(10) Patent No.: US 11,758,996 B2
(45) Date of Patent: Sep. 19, 2023

(54) METHOD FOR FACILITATING PINHOLE EFFECT AND TOOL TO MANIPULATE EYELASH SPACING FOR PINHOLE EFFECT

(71) Applicant: Vance M. Thompson, Sioux Falls, SD (US)

(72) Inventor: Vance M. Thompson, Sioux Falls, SD (US)

(*) Notice: Subject to any disclaimer, the term of this patent is extended or adjusted under 35 U.S.C. 154(b) by 1080 days.

(21) Appl. No.: 16/431,072

(22) Filed: Jun. 4, 2019

(65) Prior Publication Data
US 2020/0383448 A1      Dec. 10, 2020

(51) Int. Cl.
*A45D 2/48*      (2006.01)
*A41G 5/02*      (2006.01)
(Continued)

(52) U.S. Cl.
CPC ............... *A45D 2/48* (2013.01); *A41G 5/02* (2013.01); *A45D 40/26* (2013.01); *A61F 9/00* (2013.01);
(Continued)

(58) Field of Classification Search
CPC . A41G 5/02; A45D 2/48; A45D 40/26; A45D 40/262; A45D 40/264; A45D 7/00; A45D 24/00; A45D 24/02; A45D 24/04; A45D 24/10; A45D 24/16; A45D 24/18; A45D 24/30; A45D 34/042; A45D 34/043; A45D 2200/155
See application file for complete search history.

(56) References Cited

U.S. PATENT DOCUMENTS 4,135,527 A * 1/1979 Montiel ............... A45D 40/265
                                                             132/200
4,964,429 A * 10/1990 Cole .......................... A46D 1/00
                                                             132/218
(Continued)

FOREIGN PATENT DOCUMENTS

| JP | 2009-189734 A1 | 8/2009 |
| JP | 2009219571 | 10/2009 |
| KR | 10-0553361 | 2/2006 |

OTHER PUBLICATIONS

PCT International Preliminary Report on Patentability in International Application PCT/US2020/035821, dated Dec. 16, 2021, 6 pages.
(Continued)

*Primary Examiner* — Cris L. Rodriguez
*Assistant Examiner* — Karim Asqiriba
(74) *Attorney, Agent, or Firm* — Merchant & Gould P.C.

(57) ABSTRACT

A method of compensating for a refractive error, including manipulating eyelashes to project into a line of sight of an eye at least when an eyelid from which the eyelashes extend is partially closed or when the eye is moved relative to the eyelid. The method may further include manipulating at least one of spacing, orientation, direction, contour or shape of the eyelashes to create an optical effect that improves visual acuity when the eyelashes project into the line of sight and training an individual whose eyelashes are manipulated to position the eyelid from which the eyelashes extend, the eye or both the eyelid and the eye from which the eyelashes extend to achieve relative positioning of the eye and the eyelid to obtain the optical effect that improves visual acuity when desired.

14 Claims, 10 Drawing Sheets

(51) Int. Cl.
*A45D 40/26* (2006.01)
*G02C 3/00* (2006.01)
*A61H 5/00* (2006.01)
*A61F 9/00* (2006.01)
*G02C 7/16* (2006.01)

(52) U.S. Cl.
CPC .............. *A61H 5/00* (2013.01); *G02C 3/003* (2013.01); *G02C 7/165* (2013.01); *A61H 2201/0221* (2013.01); *A61H 2201/165* (2013.01); *A61H 2205/024* (2013.01); *G02C 2202/08* (2013.01)

(56) References Cited

U.S. PATENT DOCUMENTS

| | | | |
|---|---|---|---|
| 2002/0189628 A1* | 12/2002 | Iosilevich | A45D 2/48 132/217 |
| 2003/0102005 A1 | 6/2003 | Muraki | |
| 2008/0196732 A1* | 8/2008 | Merszei | G09B 19/00 523/105 |
| 2015/0201692 A1* | 7/2015 | Hansen | A41G 5/02 132/216 |
| 2016/0106191 A1 | 4/2016 | Dorsey | |
| 2017/0231352 A1 | 8/2017 | Horino | |
| 2017/0231368 A1 | 8/2017 | Navarro | |

OTHER PUBLICATIONS

Flint, "What do you see through the peephole?" prior to Jun. 4, 2019, 1 page.
"12 Important Things I Wish I knew before Getting Eyelash Extension" Cosmopolitan, Nov. 5, 2018,16 pages.
PCT International Search Report for International Application No. PCT/US2020/035821, dated Sep. 17, 2020, 7 pages.

* cited by examiner

METHOD FOR FACILITATING PINHOLE EFFECT AND TOOL TO MANIPULATE EYELASH SPACING FOR PINHOLE EFFECT

TECHNICAL FIELD

The invention generally relates to a method and tool for eyelash manipulation. More particularly, the invention relates to a method and tool for adjusting and fixing spacing, orientation, direction, contour or shape of the eyelashes.

BACKGROUND

The phenomenon of vision occurs because of the cooperation of many different parts of the eye. These parts of the eye and the visual system cooperate optically and on a sensory basis to enable visual perception of the world. Light passes through the cornea, the clear, convex shaped surface that is the most anterior refractive surface of the eye. The cornea refracts incoming light. The iris, the colored part of the eye, regulates the size of the pupil, the opening that controls the amount of light that enters the eye. Behind the iris and through the pupil is the lens, a clear part of the eye that further focuses light, to form an image, onto the retina. The retina is a thin, delicate, photosensitive tissue that contains the photoreceptor cells that convert light into electrical signals. Electrical signals are processed further within the retina, and then travel from the retina of the eye to the brain through the optic nerve, a bundle of about one million nerve fibers where they are further processed in the visual pathways and the visual cortex.

The mechanism of receiving and focusing light on the retina is accomplished through refraction. Refraction involves the bending of light as it passes through the cornea and the lens. The light is then focused on the retina. The retina converts the light-rays into electrical signals that are sent through the optic nerve to the brain. The brain interprets these signals into the images we see. Our eyes project information from a three-dimensional world to a basically two-dimensional surface, corresponding to the photoreceptor plane in the retina. In theory, only one plane or surface can be in focus at one time. However, the eye, like many optical systems, exhibits a certain tolerance to out-of-focus images, a feature that is known as depth-of-focus. The corresponding distance range in which the objects are seen clearly is known as depth-of-field. The ideal eye would image every light point of an object to a corresponding small point on the retina. However, focusing errors such as refractive errors and other aberrations in combination with poor depth of focus or depth of field can cause light passing through all parts of the pupil of the eye to not be accurately focused. In such instances, incoming light will fall on a spot on the retina rather than a single point, and the object will appear blurred.

Blurred images due to poor depth of focus or depth of field are commonly caused by refractive errors. Refractive errors can occur when the shape of the eye prevents lights from focusing directly on the retina. The lengths of the eyeball (longer or shorter), changes in the shape of the cornea, or aging of the lens can contribute to refractive errors. The most common types of refractive errors are myopia, hyperopia, presbyopia, and astigmatism. Myopia, or nearsightedness, is a condition where objects up close appear clearly, while objects far away appear blurry. With myopia, light comes to focus in front of the retina instead of on the retina. Hyperopia, or farsightedness, is a common type of refractive error where distant objects may be seen more clearly than objects that are near. However, people experience hyperopia differently depending upon their ability to accommodate. Some people may not notice any problems with their vision, especially when they are young. For some people with significant hyperopia, vision can be blurry for objects at any distance, near or far. Astigmatism is a condition in which the eye does not focus light evenly onto the retina, which can cause images to appear blurry and stretched out. Another common refractive error is presbyopia. Presbyopia is an age-related condition in which the ability to focus up close becomes more difficult. As the eye ages, the lens can no longer change shape enough to allow the eye to focus close objects clearly.

The number of people globally with refractive errors has been estimated at one to two billion. Rates vary among regions of the world. In general, near-sightedness is the most common disorder. How refractive errors are treated or managed depends upon the degree and severity of the conditions. Eye aberrations are commonly corrected by lenses that restore vision by altering rays before they pass through the cornea. However, many people suffering from a refractive disorder forgo a treatment option, or fail to realize that they are a candidate for a treatment option. Often those with mild refractive disorders tend to forgo contacts or glasses until their vision worsens and instead either knowingly or unknowingly squint to see more clearly.

Squinting causes the eyelids to cover a portion of the pupil thereby effectively creating a smaller aperture through which light passes to reach the retina. Squinting also is believed to slightly change the shape of the eye, and by doing so, light entering the eye may be focused more correctly onto the retina. Light traveling into the eye comes from many different angles and must be focused onto a single area at the back of the eye. Because the muscles of the eye and muscle of the surrounding eye structure, such as eyelids, contract during squinting, squinting reduces the size of the pupil which acts as the aperture stop of the eye. The small amount of increased clarity of vision employs the optical principle called "the pinhole effect".

For example, in a hyperopic eye, light from a distant point source "P" would be in focus "F" behind the cornea and thus forms a blurred circle "S" on the retina. The size of this circle, and thus the amount of blur perceived, is proportional to the degree of refractive error and the size of the pupil of the eye. A pinhole (diameter of about 1 mm) in front of the pupil (diameter of 3 to 4 mm or larger) does not alter the focus of the eye but reduces the size of the blur circles and thus improves perceived clarity of vision.

Clinically, doctors take advantage of the pinhole effect to test to determine whether reduced visual acuity is caused by refractive errors versus pathological diseases. For example, during an eye exam a doctor may administer a routine vision examination consisting of asking a patient to read an eye chart while using a pinhole occluder. An improvement in vision using a pinhole occluder as compared without the pinhole occluder may indicate that the problem is refractive in nature rather than caused by a pathological condition such as cataracts, macular degeneration, or lens clouding.

In a non-clinical setting, a common way to experience the pinhole effect is through the use of pinhole glasses or a pinhole occluder. With pinhole glasses, multiple pinholes increase the vision angle and the amount of light that reaches the retina. However, because of the multiplicity of holes, more images can occur on the retina. If two pinholes are separated by less than the diameter of the pupil aperture, two pencils of ray coming from one light point pass through the pupil and form two retinal images. Further, too large of a separation will result in dead spots in the field while too small of a separation will produce multiple images.

It is impossible to produce a separation that is optimum for all refractive defects and pupil sizes that vary both from person to person and with illumination. In some instances, use of relatively small separation may be preferable because of the reduced likelihood of localized field obscuration. Thus, pinhole glasses with carefully selected variables may be able to provide improved vision, however the time and expense associated with creating individualized pinhole glasses outweighs their advantages.

Although glasses, contacts, and pinhole glasses are all ways in which a person can correct for or compensate for refractive errors there is still room for improvement in the arts of refractive correction by use of a tool or method to the field of vision of the eye.

SUMMARY

Existing products that address refractive errors, such as contact lenses, glasses, and pinhole glasses, are some available options that provide correction or relief to refractive error sufferers. However, there are still areas in which refractive error correction tools and methods can be improved.

The example embodiments of the inventions disclosed, described and claimed herein address many of the above discussed problems and concerns.

According to an example embodiment, the invention includes a method and tool for manipulating eyelashes to optimize spacing and orientation. Eyelashes, also known as cilia, are an array of hairs located at the eyelid margin. Generally eyelashes are manipulated for vanity reasons such as making eyes appear more awake. Tools and techniques are commonly used to curl eyelashes upwards or to lengthen, thicken, and separate them. A prior art example of a tool that can be used to manipulate eyelashes is a hand-operated mechanical device such as an eyelash curler. An eyelash curler typically is curved for the natural shape of the eye and has a lower pad that is pressed against the eyelashes by an opposing narrow bar. Lashes are positioned between a top and bottom padded base and the tool is gently closed, compressing and crimping the lashes. Typically, an eyelash curler is used to crimp eyelashes upward and toward the upper eye lid, resulting in a wider and more awake looking eye. An alternative or adjunct to a mechanical tool to manipulate eyelashes is mascara. Mascara can be applied to eyelashes to increase their appearance of thickness, length and/or separation.

According to an example embodiment of the invention, eyelashes are manipulated in order to manipulate spacing and orientation to improve visual acuity. According to an example embodiment, eyelashes can be manipulated to decrease exposure of the eye to environmental factors such as light. For example, according to an example embodiment of the invention, eyelashes are manipulated to be positioned more readily in a person's field of vision. Manipulation of eyelashes may decrease a person's field of vision and may decrease the amount of light entering a person's eye. It is expected that decreasing light received by the retina by manipulation of eyelashes according to an example embodiment will improve visual acuity by taking advantage of pinhole or diffractive optical effects. According to an example embodiment, manipulation of eyelashes creates effects similar to those observable with pinhole glasses and/or a pinhole occluder. According to an alternative example embodiment, it is expected that a method of manipulating eyelashes can create conditions necessary to induce single slit diffraction or other diffractive effects to improve focusing.

To better define the concepts of the invention, applicant defines the following terms: diffraction and single slit diffraction.

Diffraction is defined as the slight bending of light as it passes around the edge of an object. The amount of bending depends on the relative size of the wavelength of light to the size of the opening. If the opening is much larger than the light's wavelength, the bending will be almost unnoticeable. However, if the two are closer in size or equal, the amount of bending is considerable, and easily seen with the naked eye.

Single-slit diffraction is one of the most fundamental concepts involving diffraction. When a light propagates through a slit or aperture, the result depends upon the physical size of the aperture with respect to the wavelength of the incident of the beam. Assuming a coherent, monochromatic wave emitted from as point source "S", passes through aperture "d" and is diffracted. When the wavelength "k" is much smaller than the aperture width "d", the wave travels onward in a straight line, just as it would if it were a particle or no aperture were present. However, when the wavelength exceeds the size of the aperture, diffraction of the light is represented by the following equation:

$$\sin \theta = \lambda/d$$

wherein $\theta$ is the angle between the incident central propagation direction and the first minimum of the diffraction pattern.

According to an example embodiment of the invention, eyelashes are manipulated with different techniques, mechanical tools and methods. A tool according to an example embodiment of the invention may include any of a variety of lash manipulators. For example, tools may include a structure similar to but different from a lash curler or straightener. According to another example embodiment, a tool may include a structure similar to a lash comb or bristle lash brush. According to another example embodiment, a tool may be include a hybrid lash curler or straightener with an attached lash comb or bristle component. According to an example embodiment of the invention, a tool can be used to simultaneously bend or straighten lashes while spacing them to achieve a desired effect.

An example embodiment of the invention includes a method of compensating for a refractive error, including manipulating eyelashes to project into a line of sight of an eye at least when an eyelid from which the eyelashes extend is partially closed or when the eye is moved relative to the eyelid; further manipulating at least one of spacing, orientation, direction, contour or shape of the eyelashes to create a optical effect that improves visual acuity when the eyelashes project into the line of sight; and training an individual whose eyelashes are manipulated to position the eyelid from which the eyelashes extend, the eye or both the eyelid and the eye from which the eyelashes extend to achieve relative positioning of the eye and the eyelid to obtain the optical effect that improves visual acuity when desired.

The example method may further include applying a lash setting material to the eyelashes.

The example method may further include applying a fibrous substance to the lashes to assist in setting the lashes. The fibrous material may be applied generally parallel to or generally perpendicular to the normal extension of the natural eyelashes. In this context, parallel and perpendicular should be broadly interpreted beyond their precise geometric meaning in view of the non-rectilinear linear nature of natural eyelashes. For example, the fibrous material may be applied transverse to the eyelashes to facilitate a pinhole or diffractive effects. According to another example embodiment, fibrous material may be applied to extend the length of the eyelashes to facilitate extension into the line of sight. Fibrous material utilized for extending the length of the eyelashes may include naturally occurring materials such as hairs from the mink or other animals or plant-based materials such as cellulose fibers as well as synthetic materials. Silk may be utilized as well. Any materials that are utilized in the application of cosmetic eyelash extensions can be utilized as well according to example embodiments of the invention.

According to another example aspect of the invention, false eyelashes may be utilized as well. False eyelashes differ from eyelash extensions in that they are generally adhered to the eyelid rather than to the eyelashes and in that they are generally made to extend across most of the width of the eyelid. According to example embodiments of the invention, contrary to the known prior art, the false eyelashes extend downwardly from the upper eyelid or upwardly from the lower eyelid into the eye line of sight rather than being curled as in cosmetic false eyelashes.

The example method may further include inserting micro lenses between or applying microlenses to the eyelashes.

The example method may further include manipulating spacing between the eyelashes to take advantage of a pinhole effect to improve visual acuity. This may include creating pinhole apertures or slit apertures or both between the upper eyelashes the lower eyelashes or both.

The example method may further include manipulating spacing between the eyelashes to create diffractive optical effects to improve visual acuity. This may include creating pinhole apertures or slit apertures or both between the upper eyelashes the lower eyelashes or both.

The example method may further include manipulating the eyelashes with a lash manipulating tool.

The example method may further include curling the upper eyelashes downward.

The example method may further include applying a grid of material to the upper eyelashes to create multiple pinholes or slits between the eyelashes.

The example method may further include making or selecting the lash setting material to comprise a wax, an adhesive or a gel.

The example method may further include applying the lash setting material in combination with a fiber material or a fiber grid material.

The example method may further include applying heat to the eyelashes to assist in "setting" the lashes in a desired orientation and spacing thereby creating pinhole apertures or slit apertures between or among the eyelashes.

According to an example embodiment, a method for manipulating eyelashes includes crimping and/or straightening eyelashes with a mechanical lash-manipulating tool. In some aspects a mechanical lash-manipulating tool includes at least one handle and an upper and lower portion. In some example aspects a lash-manipulating tool can further include a removable lash insert with indentations.

According to an example embodiment of the invention, a method of manipulating eyelashes can include positioning eyelashes between a top surface and an indented bottom insert and closing the tool to compress the eyelashes. In some aspects compression of the eyelash manipulating tool without a removable lash insert crimps eyelashes outward away from the lash base and down into a person's field of vision. In some aspects compression of the eyelash manipulating tool with a removable lash insert crimps eyelashes outward away from the lash base and down into a person's field of vision while also compressing an area of eyelash in contact with the removable lash insert.

It is expected that eyelashes can be manipulated by curling them downward or straightening them in a downward orientation in order to increase or decrease exposure of the eye to environmental factors such as light. For example, eyelashes can be manipulated to be positioned in a person's field of vision. Manipulation of eyelashes can decrease a person's field of vision and may decrease the amount of light entering a person's eye. It is expected that manipulation of eyelashes according to the example embodiments will decrease the amount of light entering a person's eye and improve vision acuity by inducing slit diffraction of light and/or a pinhole effect.

A method and tool for manipulating eyelashes according to an alternative example embodiment can further include eyelash application substances such as a bio-acceptable lash setting product, a lash grid material or substance and/or a micro lens. According to an example embodiment, an eyelash application substance(s) can be used with or without use of the lash-manipulating tool.

According to another example embodiment, a bio-acceptable lash setting product can include for example, a wax, adhesive or gel that can be used to "set" lashes in their manipulated state. The setting product can be applied with a lash brush or any other brush or applicator suitable for application of a bio-acceptable product to lashes. In some aspects, a lash setting product can be applied to eyelashes after a lash manipulating tool according to an example embodiment of the invention has been used. In some aspects, a lash setting product can be applied to bare lashes. According to an example embodiment of the present invention, the lash setting product can be used to set eyelashes after the product is applied. In some aspects, application of a lash setting product holds lashes in an oriented or manipulated position.

According to an example embodiment, an eyelash application substance can include a lash grid material or substance. In some aspects a lash grid solution is a bio-acceptable solution that contains a fiber or fibrous component. In some aspects the lash grid solution can be applied to bare eyelashes or eyelashes coated with a lash setting product. In some aspects, when a lash grid solution is applied to eyelashes the fibrous component attaches to the eyelashes. In some aspects the fibrous component of the lash grid solution thickens lashes. In some other aspects, application of the fibrous component to the eyelashes creates a "grid-like" structure on the lashes. According to another example embodiment of the invention, a grid, mesh or screen is applied to the eyelashes. According to a further example embodiment, artificial or simulated eyelashes may be included in between the natural eyelashes.

According to another example embodiment of the invention, lashes can be manipulated by including a bio-acceptable material on and/or between the eyelashes to aid in focusing of light. According to an embodiment, this material may include a micro lens.

According to an example embodiment of the present invention, a method for optimizing lash spacing includes a lash manipulating tool is used to crimp lashes, optional application of a lash setting product, optional application of a lash grid substance or material, optional application of artificial eyelashes, optional application of a grid, mesh or screen and option application of a micro lens.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
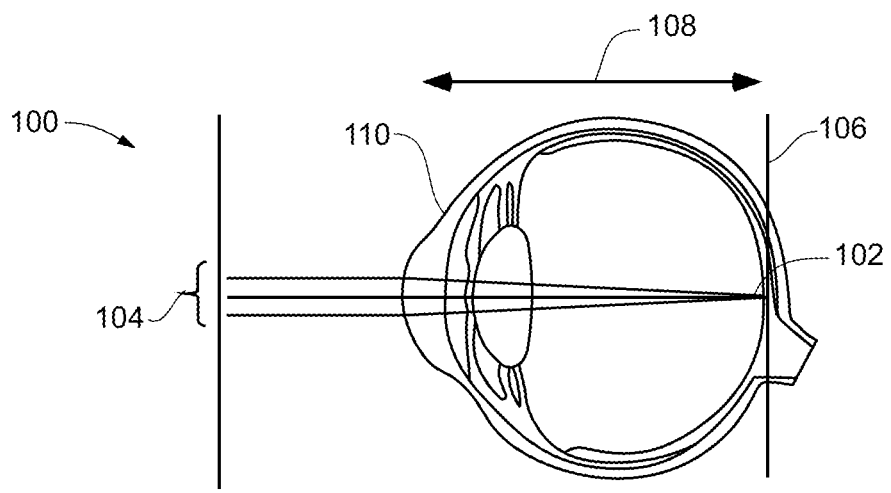
FIGS. 1A-1C are a cross sectional views of an eye demonstrating several refractive errors.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1B:
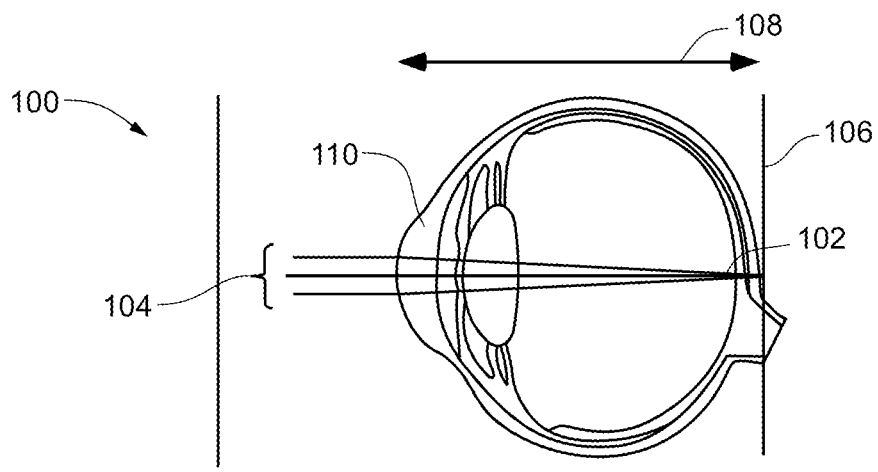

Referring to FIG. 1A, eye 100 without refractive error images light rays 102 on retina 104. Accordingly, light is imaged and focused at the retina without the need for refractive correction. Generally, vision can be affected by refractive errors such as, for example, hyperopia and myopia. Referring to FIG. 1B, hyperopia causes light 102 to be focused at focal point 106 behind the retina because focal length 108 of optical parts 110 of the eye is longer than the length of the globe of the eye.

Figure 1C:
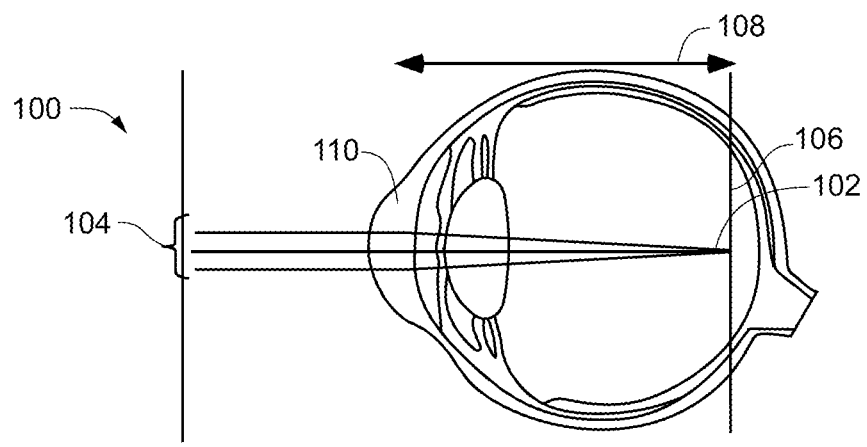

Referring to FIG. 1C, myopia causes light rays 102 to be focused at a focal point 106 in front of the retina because focal length 108 of optical parts 110 of eye 100 is shorter than the length of globe of the eye 100. Both refractive errors as well as other refractive errors may cause blurred vision and/or other focusing difficulties and require correction. Corrective lenses, methods or devices to correct the refractive error and restore normal vision are known.

According to an example embodiment of the invention, refractive errors can be mitigated by manipulation of eyelashes 112. Eyelash manipulators 114 including eyelash curlers and various brushes or combs are known in the art but the structures, so far as Applicant is aware, are uniformly made to curl eyelashes 112 upwardly for aesthetic appeal. Examples of prior art eyelash manipulators 114 are depicted in FIGS. 2-4.

Figure 2:
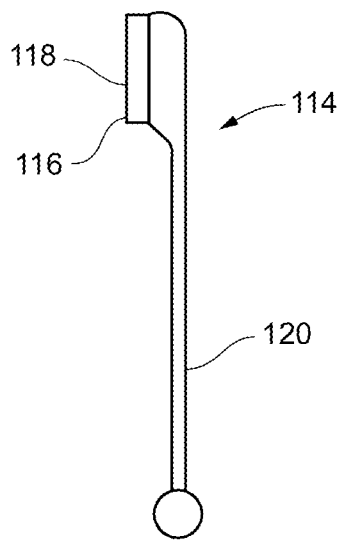
FIG. 2 is a perspective view of a prior art tool.

Referring to FIG. 2, prior art eyelash manipulator 114 includes lash separating structures 116 such as straight or curved metal comb 118 and handle 120 that may be foldable for ease of storage.

Figure 3:
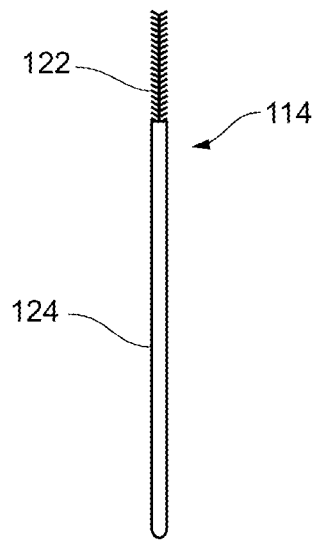
FIG. 3 is a perspective view of a prior art tool.

According to FIG. 3, prior art eyelash manipulator 114 according to the prior art, may alternatively include fibrous bristles 122 and straight handle 124. Compared to the rigid and straight lash separating mechanism 202 as depicted in FIG. 2, lash separating mechanism 116 has a spoolie shape and is softer on eyelashes 112.

Figure 4:
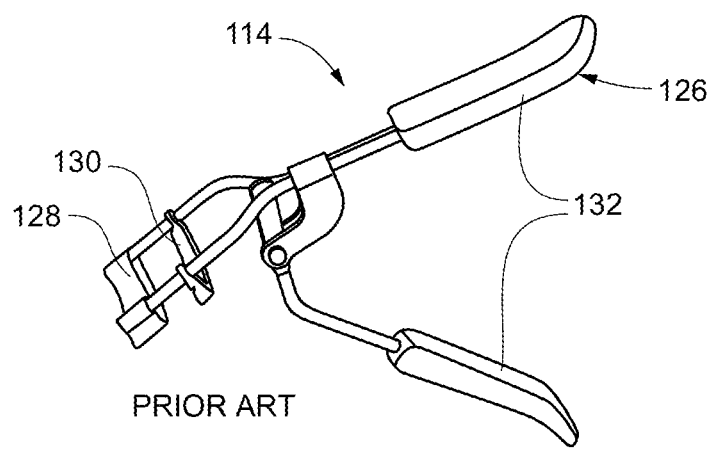
FIG. 4 is a perspective view of an eyelash manipulator tool according to the prior art.

Referring now to FIG. 4, according to the prior art, eyelash curler 126 can be used to manipulate eyelashes and curl them upward for aesthetic appearance. Generally eyelash curler 126 includes upper rigid curved top 128 and lower curved resilient padded base 130, and two mutually opposed handles 132. In use, eyelashes are positioned between rigid curved top 128 and padded base 130 and opposed handles 132 are opened to admit eyelashes 112 and then closed like a pair of scissors. Closing of opposed handles 132 forces upper rigid curved top 128 and resilient padded base 130 together, thereby crimping eyelashes 112 upwardly.

Figure 5:
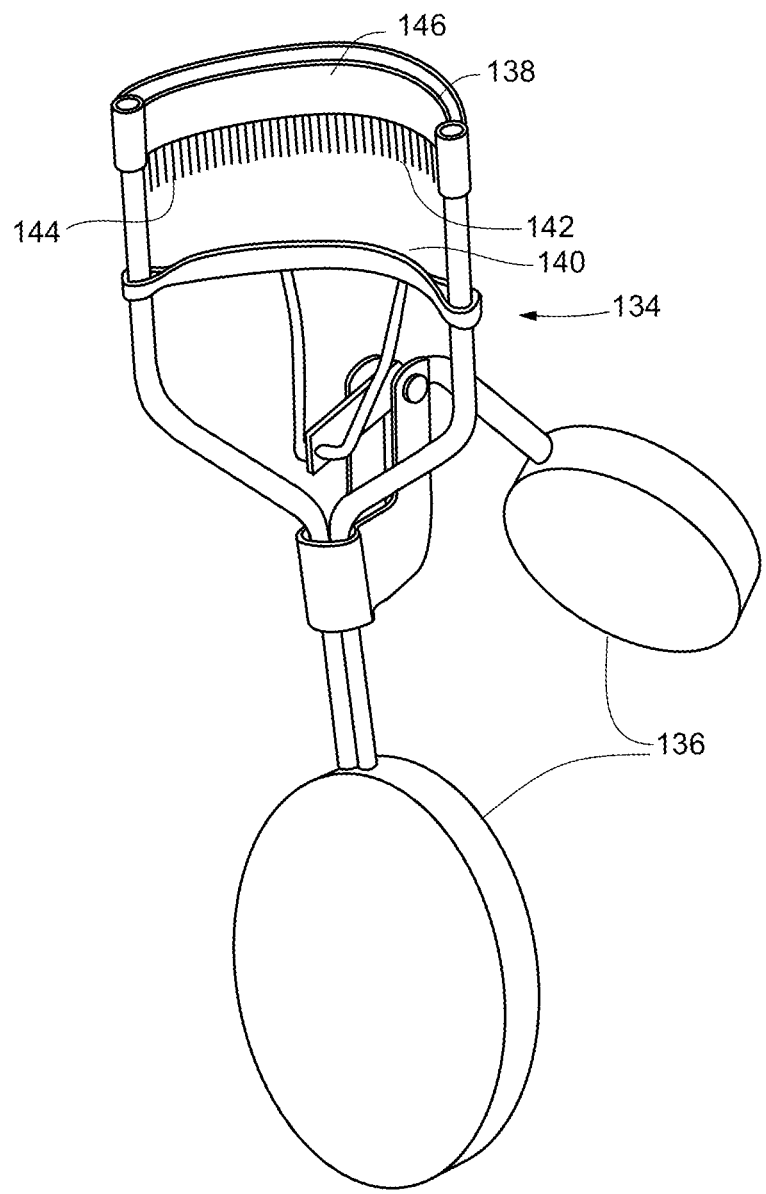
FIG. 5 is a perspective view of an eyelash manipulator tool according to an alternative example embodiment of the invention.

Referring now to FIG. 5, eyelash manipulator 134 according to an example embodiment of the invention includes handles 136, upper curved resilient padded base 138 and curved bar 140, and optionally, removable toothed insert 142.

In the depicted embodiment, curved bar 140 is slidably movable between a first position located away from upper curved resilient padded base 138 and a second position in contact with upper curved resilient padded base 138. Removable or optional toothed insert 142 may be coupled to either upper curved resilient padded base 138 or curved bar 140. Teeth 144 of removable toothed insert 142 may be sized and spaced to create a desired size of pinhole space between eyelashes 112 when utilized. Removable toothed insert 142 and/or upper curved resilient padded base 138 may further include reservoir 146 containing lash setting material. When curved bar 140 contacts upper curved resilient padded base 138 indents upper curve resilient padded base 138 because of the resiliency thereof. Handles 136 are linked to curved bar 140 and upper curved resilient padded base 138 to accomplish slidable or other movement of the two parts relative to one another.

Figure 6:
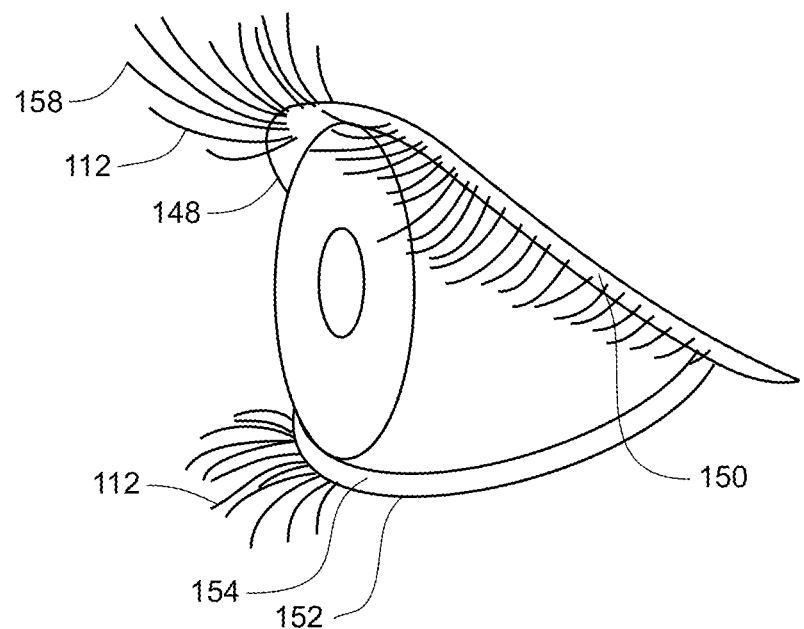
FIG. 6 is a perspective schematic view of an eye and eyelashes in their un-manipulated orientation.

Referring to FIG. 6, in the schematic depiction under normal circumstances eyelashes 112 of upper eyelid 148 generally extend outwardly and upwardly from upper eyelid margin 150. Eyelashes 112 of the lower eyelid 152 generally extend it outwardly and downwardly from lower eyelid margin 154. While the example embodiments presented in this application generally refer to the upper eyelashes, it should be understood that the invention may be applied to the lower eyelashes as well so that the upper eyelashes may be manipulated, the lower eyelashes may be manipulated or both may be manipulated.

Figure 7:
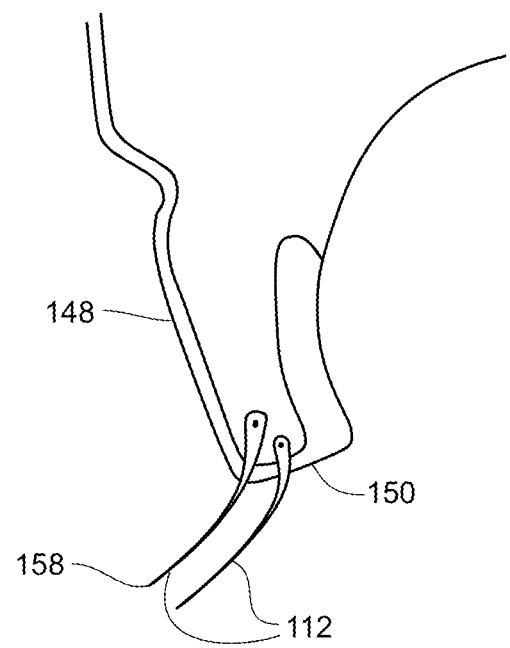
FIG. 7 is a cross-sectional schematic view of an eyelid and eyelashes in their unmanipulated orientation.

Referring to FIG. 7, in a cross-sectional view of upper eyelid 148 it can be seen that, under normal circumstances, upper eyelid margin 150 is a roughly planar structure from which eyelashes 112 of upper eyelid 148 extend. While eyelashes 112 exit upper eyelid margin 150 in a generally downward and outward direction, the normal curvature of eyelashes 112 generally causes eyelashes of central portion 156 to extend outwardly and upwardly at their distal terminus 158.

Figure 8:
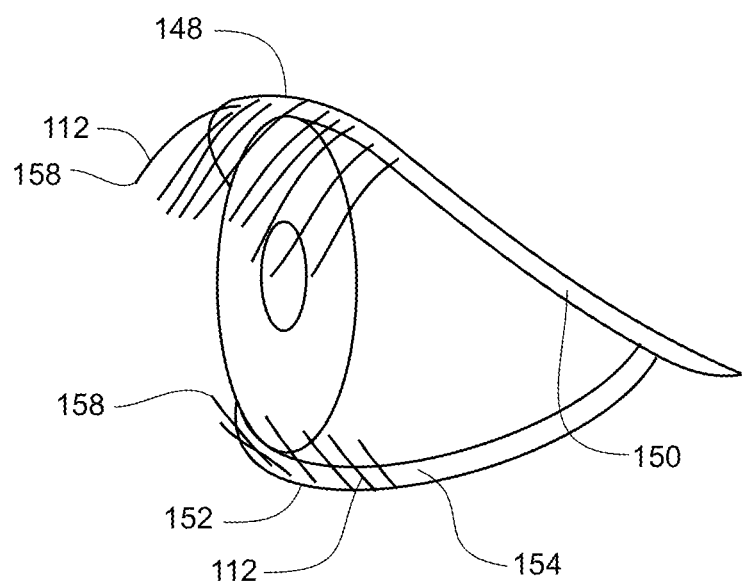
FIG. 8 is a perspective schematic view of an eye and lie lashes having been manipulated in accordance with an example embodiment of the invention.

Referring to FIG. 8, according to an example embodiment of the invention at least central upper eyelashes 160 of upper eyelid 148 are manipulated to extend generally downwardly so that central upper eyelashes 160 of upper eyelid 148 extend into visual axis 162 which extends outwardly from eye 100 at least when upper eyelid 148 and eye 100 are moved relatively closer together by movement of either eye 100 or upper eyelid 148 or both.

Figure 9:
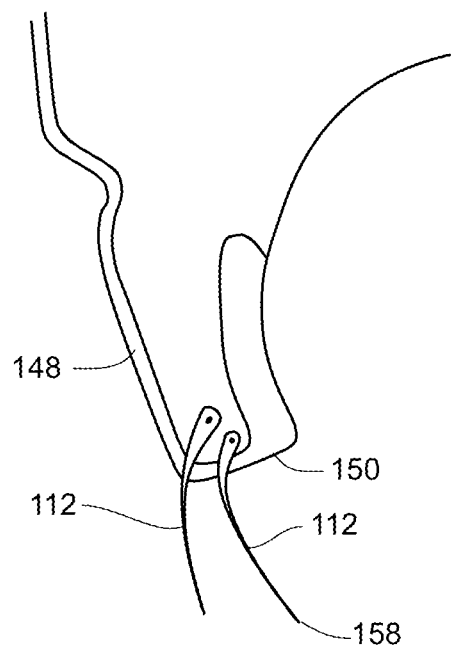
FIG. 9 is a cross-sectional schematic view of an eyelid and eyelashes having been manipulated according to an example embodiment of the invention.

Referring to FIG. 9, central upper eyelashes 160 are depicted after having been manipulated according to an example embodiment of the invention to extend into the visual axis 162 as desired by a patient under at least some circumstances.

Figure 10:
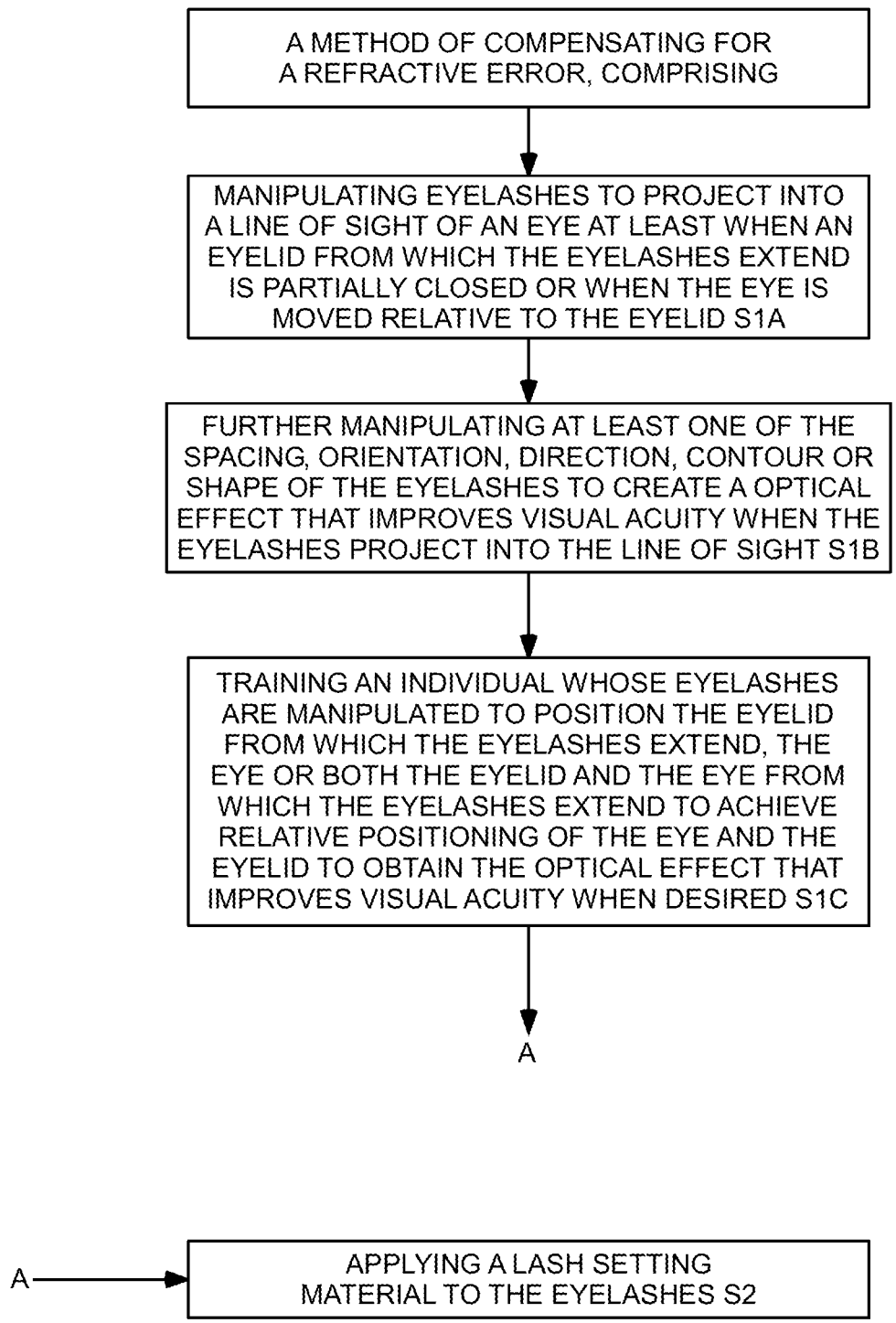
FIG. 10 is a flow chart of the method according to an example embodiment of the invention.
Figure 10:
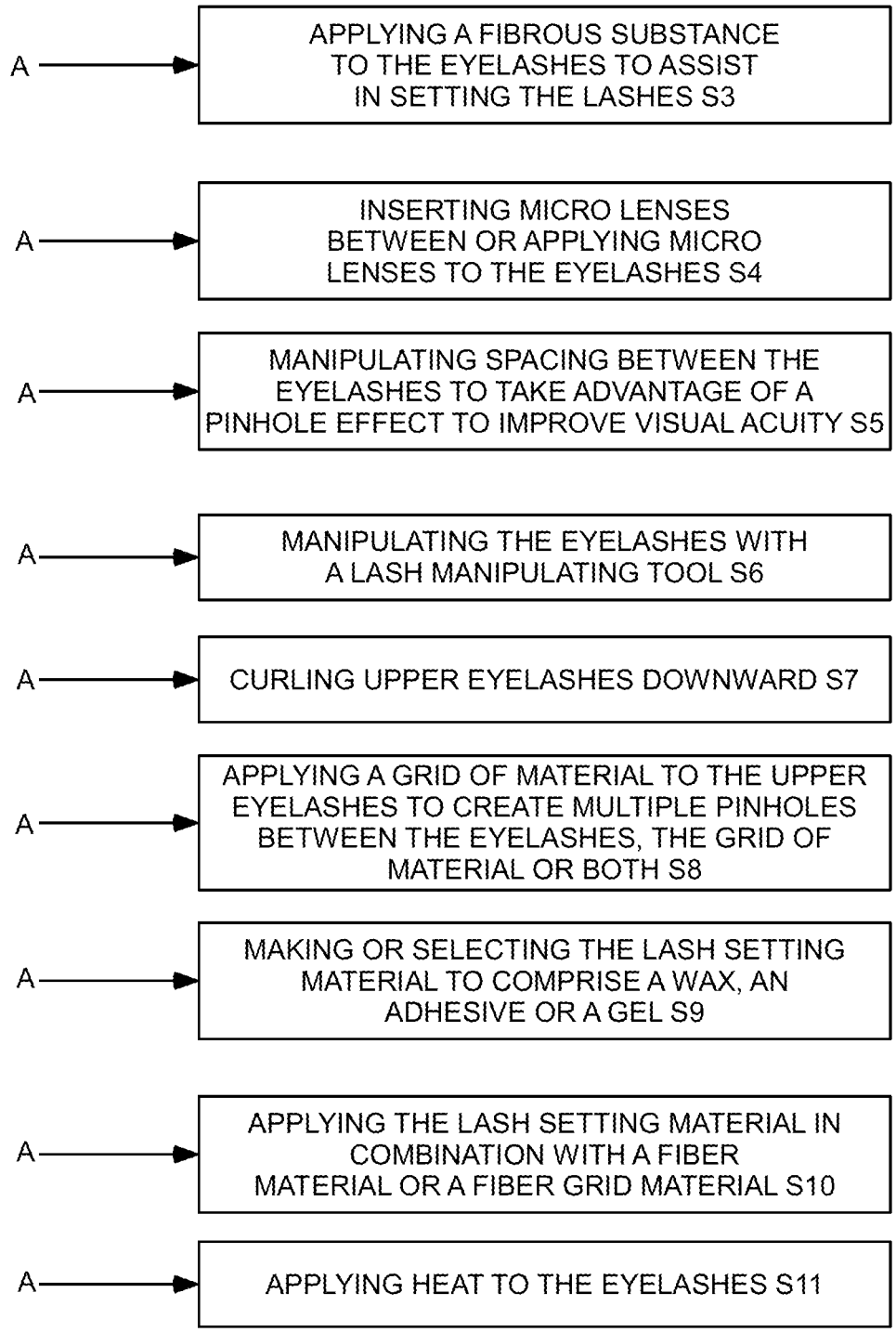

According to another example embodiment of the invention, with reference to FIG. 10, a method for compensating for refractive error S1 includes: manipulating eyelashes to project into a line of sight of an eye at least when an eyelid from which the eyelashes extend is partially closed or when the eye is moved relative to the eyelid S1A; further manipulating at least one of spacing, orientation, direction, contour or shape of the eyelashes to create an optical effect that improves visual acuity when the eyelashes project into the line of sight S1B; and training an individual whose eyelashes are manipulated to position the eyelid from which the eyelashes extend, the eye or both the eyelid and the eye from which the eyelashes extend to achieve relative positioning of the eye and the eyelid to obtain the optical effect that improves visual acuity when desired S1C.

According to another example embodiment of the invention, the method further includes applying a lash setting material to the eyelashes. S2

According to another example embodiment of the invention, the method further includes applying a fibrous substance to the eyelashes to assist in setting the eyelashes. S3 The fibrous material may be applied generally parallel to or generally perpendicular to the normal extension of the natural eyelashes. In this context, parallel and perpendicular should be broadly interpreted beyond their precise geometric meeting in view of the non-rectilinear linear nature of natural eyelashes. For example, the fibrous material may be applied transverse to the eyelashes to facilitate a pinhole or diffractive effects. According to another example embodiment, fibrous material may be applied to extend the length of the eyelashes to facilitate extension into the line of sight. Fibrous material utilized for extending the length of the eyelashes may include naturally occurring materials such as hairs from the mink or other animals or plant-based materials such as cellulose fibers as well as synthetic materials. Silk may be utilized as well. Any materials that are utilized in the application of cosmetic eyelash extensions can be utilized as well according to example embodiments of the invention.

According to another example aspect of the invention, false eyelashes may be utilized as well. False eyelashes differ from eyelash extensions in that they are generally adhered to the eyelid rather than to the eyelashes and that they are generally made to extend across most of the width of the eyelid. According to example embodiments of the invention, contrary to the known prior art, the false eyelashes extend downwardly from the upper eyelid or upwardly from the lower eyelid into the eye line of sight rather than being curled as in cosmetic false eyelashes.

According to another example embodiment of the invention, the method further includes inserting micro lenses between or applying micro-lenses to the eyelashes. S3

According to another example embodiment of the invention, the method further includes manipulating spacing between the eyelashes to take advantage of a pinhole effect to improve visual acuity. S4

According to another example embodiment of the invention, the method further includes manipulating spacing between the eyelashes to create diffractive optical effects to improve visual acuity. S5

According to another example embodiment of the invention, the method further includes manipulating the eyelashes with a lash manipulating tool. S6

According to another example embodiment of the invention, the method further includes curling upper eyelashes downward. S7

According to another example embodiment of the invention, the method further includes applying a grid of material to the upper eyelashes to create multiple pinholes between the eyelashes, the grid of material or both. S8

According to another example embodiment of the invention, the method further includes making or selecting the eyelash setting material to comprise a wax, an adhesive or a gel. S9

According to another example embodiment of the invention, the method further includes applying the last setting material in combination with a fiber material or a fiber grid material. S10

According to another example embodiment of the invention, the method further includes applying heat to the eyelashes to facilitate setting in a desired position. S11

Figure 11:
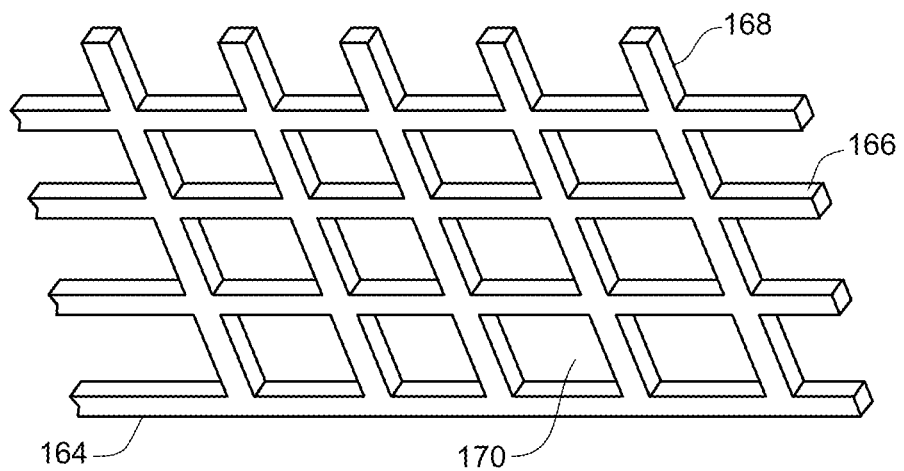
FIG. 11 is a schematic depiction of a grid structure according to an example embodiment of the invention.

Referring to FIG. 11, grid structure 164 according to an example embodiment of the invention is depicted. Grid structure 164 may be applied to central upper eyelashes 160 thereby further facilitating desirable pinhole effect. Grid structure 164 may include for example horizontal grid members 166 and vertical grid members 168.

Figure 12:
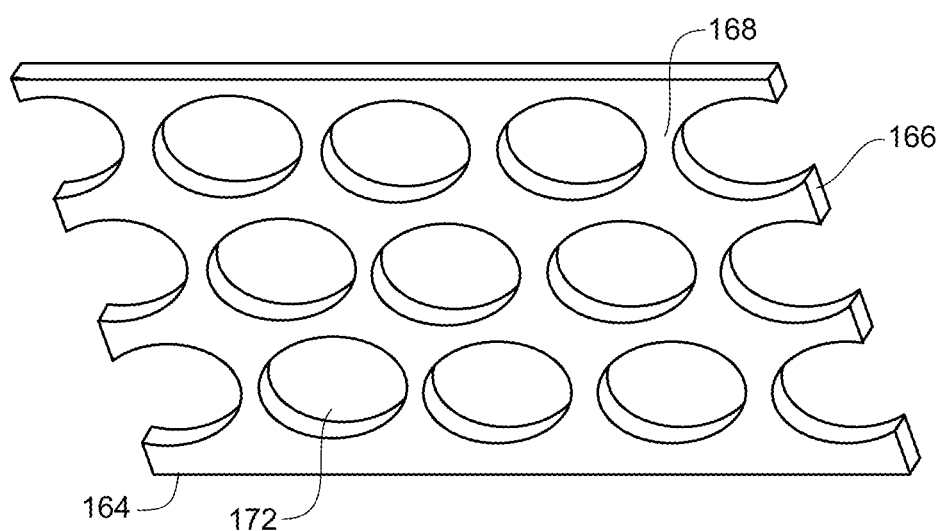
FIG. 12 is a schematic of a grid structure with defined apertures located within the grid according to an example embodiment of the invention.

Referring to FIG. 12, grid structure 164 according to an example embodiment of the invention may further include aperture structures 170. Aperture structures 170 may for example include structures defining a central circular aperture 172. Central circular apertures 172 may for example have an internal diameter of between 0.8 and 2.0 mm according to an example embodiment of the invention; between 0.5 and 1.5 mm according to another example embodiment between 0.2 1.0 m according to a further example embodiments. Central circular apertures 172 may be of a consistent size or may be of variable sizes according to example embodiments of the invention.

Figure 13:
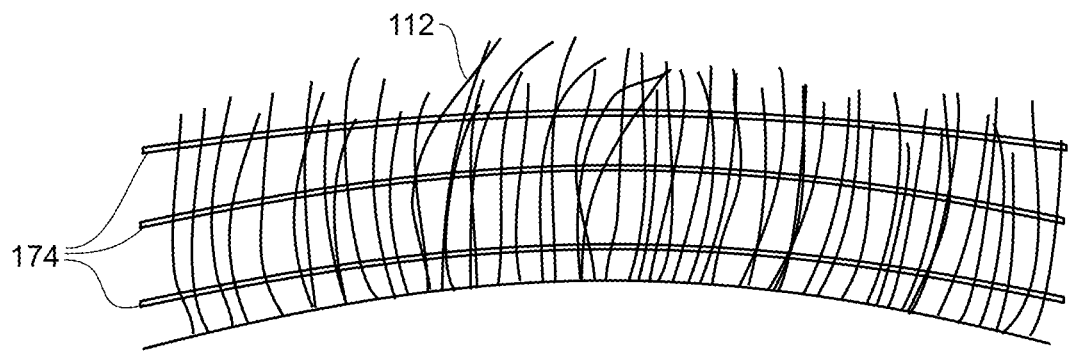
FIG. 13 depicts a series of horizontal fibers applied across the natural eyelashes according to an example embodiment of the invention.

Referring to FIG. 13, a series of horizontal fibers 174 are depicted as applied across natural central upper eyelashes 160 according to an example embodiment of the invention. Horizontal fibers 174 may be secured to natural central upper eyelashes 160 by a lash setting compound as discussed elsewhere in this application.

Figure 14:
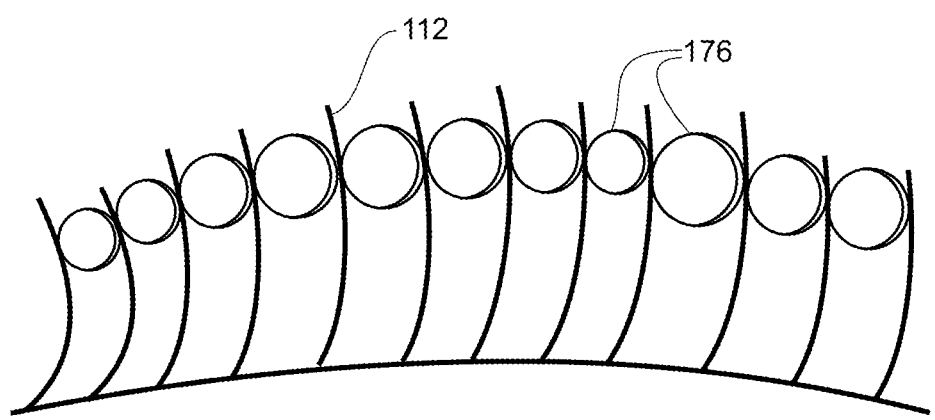
FIG. 14 depicts a series of micro-lenses placed between the natural eyelashes according to an example embodiment of the invention.

Referring to FIG. 14 according to an example embodiment of the invention, micro-lenses 176 may be inserted on between or adjacent to upper eyelashes 112 or central upper eyelashes 160. Micro-lenses 176 may range widely in power depending upon a desired optical result. For example, micro-lenses for reading distance or intermediate distance may have a power in a range of between +0.75 diopters and +3.50 diopters according to an example embodiment of the invention.

Figure 15:
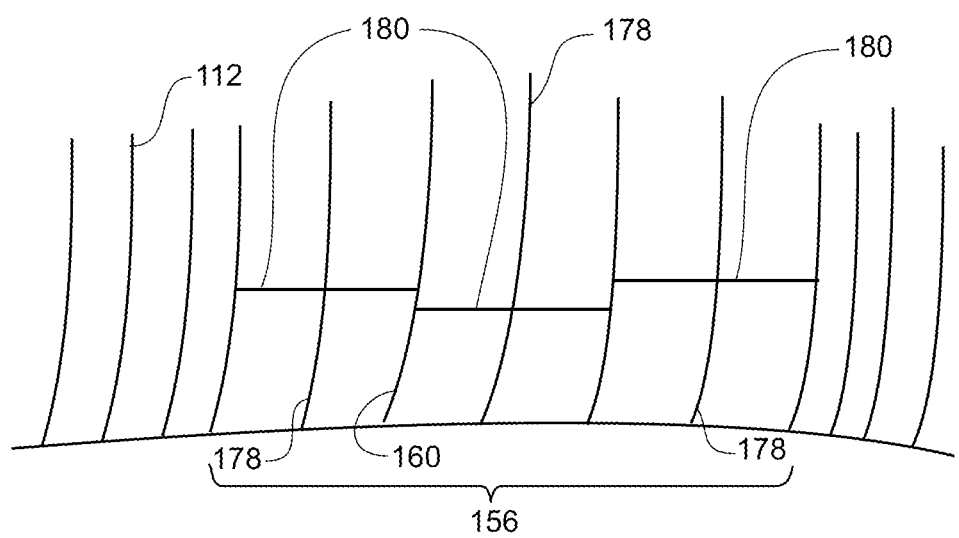
FIG. 15 depicts artificial eyelashes inserted between the natural eyelashes and supported in place by bridging structures according to an example embodiment of the invention.

Referring to FIG. 15, according to another example embodiment of the invention, two or more false or simulated eyelashes 178 may be inserted adjacent to or between central upper eyelashes 160 and supported by bridges 180 inserted between natural central upper eyelashes 160. Accordingly desired spaces between a combination of false or simulated eyelashes 178 and central upper eyelashes 160 are created. Bridges 180 may be inserted between central upper eyelashes 160 for example of the upper eyelid as well as eyelashes 112 peripherally located or of the lower eyelid. Further false or simulated eyelashes 178 may either envelop eyelashes 112 or be located between eyelashes 112 to facilitate a pinhole effect, slid a fact or diffractive sled of fact to facilitate reading an intermediate vision. Reading vision is generally considered to be vision at a working distance between 33 and 45 cm while intermediate vision is generally considered to be approximately arm's length. These distances should not be considered to be limiting.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of compensating for a refractive error, comprising:
   manipulating eyelashes on an individual to project into a line of sight of an eye at least when an eyelid from which the eyelashes extend is partially closed or when the eye is moved relative to the eyelid, wherein manipulating the eyelashes includes curling upper eyelashes downward;
   further manipulating at least one of spacing, orientation, direction, contour or shape of the eyelashes on the individual to create a space between the eyelashes;
   inserting an aperture structure containing a circular aperture into the space to create an optical effect that improves visual acuity when the eyelashes containing the circular aperture project into the line of sight; and
   providing a training instruction to the individual to position at least one of the eyelid and the eye such that the manipulated eyelashes containing the circular aperture project into the individual's line of sight to obtain the optical effect that improves visual acuity when desired.

2. The method as claimed in claim 1, further comprising applying a lash setting material to the eyelashes after inserting the aperture structure.

3. The method as claimed in claim 2, further comprising making or selecting the lash setting material to comprise a wax, an adhesive or a gel.

4. The method as claimed in claim 3, further comprising applying the lash setting material in combination with a fiber material or a fiber grid material applied to the lashes.

5. The method as claimed in claim 1, further comprising applying a fibrous substance to the eyelashes to assist in setting the lashes or to assist in creating the optical effect.

6. The method as claimed in claim 1, further comprising applying heat to the eyelashes.

7. The method as claimed in claim 1, further comprising applying simulated eyelash components in between the eyelashes along with bridging structures supporting the simulated eyelash components between the eyelashes.

8. The method as claimed in claim 1, further comprising applying false eyelashes or lash extensions proximate to or to the eyelashes.

9. The method as claimed in claim 1, wherein the aperture structure is inserted between central upper eyelashes.

10. The method of claim 1, wherein the circular aperture has an internal diameter of between 0.8 and 2.0 mm.

11. The method of claim 1, wherein the circular aperture has an internal diameter of between 0.5 and 1.5 mm.

12. The method of claim 1, wherein the circular aperture has an internal diameter of between 0.2 and 1.0 mm.

13. The method of claim 1, further comprising:
   creating an additional one or more spaces between the eyelashes; and
   further inserting additional circular aperture structures in each of the additional one or more spaces created in the eyelashes.

14. The method of claim 13, wherein the additional circular aperture structures are different in size.

* * * * *